United States Patent [19]

Ishiguro et al.

[11] Patent Number: 5,131,393
[45] Date of Patent: Jul. 21, 1992

[54] ULTRASOUND INTERNAL EXAMINATION SYSTEM

[75] Inventors: Masaaki Ishiguro; Toshizumi Tanaka; Yukio Takagi, all of Omiya, Japan

[73] Assignee: Fuji Photo Optical Co., Ltd., Omiya, Japan

[21] Appl. No.: 718,641

[22] Filed: Jun. 21, 1991

[30] Foreign Application Priority Data

Jun. 25, 1990 [JP] Japan ................... 2-164245

[51] Int. Cl.$^5$ ................................. A61B 8/00
[52] U.S. Cl. ...................... 128/660.09; 128/662.06
[58] Field of Search ............ 128/660.09, 660.10, 128/662.06, 4

[56] References Cited

U.S. PATENT DOCUMENTS

| | | | |
|---|---|---|---|
| 4,034,744 | 7/1977 | Goldberg | 128/660.09 |
| 4,047,520 | 9/1977 | Soldner et al. | 128/660.09 |
| 4,722,345 | 2/1988 | Ueno et al. | 128/660.09 |
| 4,802,487 | 2/1989 | Martin et al. | 128/662.06 |
| 4,880,009 | 11/1989 | Yanagawa | 128/660.09 |
| 4,892,103 | 1/1990 | Ogasawara | 128/660.09 |
| 4,917,096 | 4/1990 | Englehart et al. | 128/660.10 |

Primary Examiner—Francis Jaworski
Assistant Examiner—George Manuel
Attorney, Agent, or Firm—Oblon, Spivak, McClelland, Maier & Neustadt

[57] ABSTRACT

Described herein is an ultrasound internal examination system which essentially includes: an ultrasound probe having an ultrasound vibratory element at the tip end of a flexible cable to be passed through a biopsy channel of an endoscope; an operating unit detachably mounted at the rear end of the biopsy channel of the endoscope and connected to a base end portion of the flexible cable; a probe operating member provided on the operating unit to scan the ultrasound vibratory member over a predetermined scanning range; an initial position sensor means for detecting the position of an initial point of the scanning range; and an incremental encoder adapted to generate pulse signals at a predetermined frequency upon detection of and during a displacement of the ultrasound vibratory element caused by the probe operating member.

4 Claims, 6 Drawing Sheets

ULTRASOUND INTERNAL EXAMINATION SYSTEM

BACKGROUND OF THE INVENTION

1. Field of the Invention

This invention relates to an ultrasound internal examination system employing an ultrasound vibratory element to be inserted, for example, into a human body by way of an endoscope or the like for scanning a particular range of concern for inspection or for diagnostic purposes.

2. Description of the Prior Art

The ultrasound examination systems which have been widely used in medical fields generally includes an ultrasound vibratory element and an ultrasound image observation terminal which is largely constituted by ultrasound signal transmission and reception circuits, a signal processor including circuits for processing ultrasound echo signals received by the reception circuit, and a monitor for displaying an ultrasound image on the basis of the output signal of the signal processor.

It has been known in the art to insert an ultrasound vibratory element into a patient's body to a position close to a target portion of examination or diagnosis for the purpose of improving the accuracy and functions of the ultrasound examination and diagnosis. For instance, U.S. Pat. No. 4,802,487 discloses an ultrasound probe which has a single-element ultrasound transducer at the tip end of a narrow flexible cable. Through a biopsy channel which is provided in an endoscope for insertion of forceps or other instruments, the ultrasound probe is inserted into a patient's body, protruding the ultrasound transducer at the tip end of the probe from the fore end of an insert portion of the endoscope to contact an intracavitary wall such as an alimentary tract wall or the like or to confront an intracavitary wall through an ultrasound transmissive medium thereby to transmit ultrasound pulses into the body while receiving return echo signals. The ultrasound probe is scanned in a linear or radial direction manually or by a drive means like a motor to obtain a B-mode ultrasound image.

This ultrasound probe arrangement makes it possible to obtain a cross-sectional image of intracavitary wall tissues of interest in addition to endoscopic examination and diagnosis, permitting three-dimensional examination for diagnosis of high accuracy.

In this connection, the ultrasound transducer element needs to be scanned to get a B-mode ultrasound image. However, for this purpose, the single-element ultrasound transducer has to be moved mechanically by pulling the flexible cable back and forth in the linear direction or by turning the transducer in the radial direction. At this time, it is necessary to generate an ultrasound pulse in a predetermined pitch and, for determining the display position of each acoustic line of the ultrasound image to be shown on the monitor on the basis of the ultrasound return echo signal, to obtain the information indicative of the position of the ultrasound transducer in scanning. In this regard, the above-mentioned prior art employs a potentiometer in a position sensor mechanism for detecting the position of the ultrasound transducer element. For example, in linear scanning, a contact member is provided at the proximal end of the ultrasound probe in contact with a resistor of the potentiometer, sliding the contact member along the resistor as the ultrasound probe is manipulated back and forth and detecting the position of the ultrasound transducer in the scanning stroke by way of a voltage signal proportionate to the variation in resistance.

The above-mentioned potentiometer, which produces a voltage or analog signal as a measure of the transducer position, has an inherent drawback that it is apt to be influenced by voltage fluctuations in the power supply and external noises. Besides, when detecting the transducer position on the basis of the voltage signal from the potentiometer, the output signal is compared by a comparator to determine a difference in voltage level. Therefore, in order to enhance the resolution of distance, such voltage level differences of comparison have to be minimized. For example, in a case where the full scanning stroke range is 20 mm and ultrasound signal of about 500 pulses is transmitted in that range, the pulse intervals become extremely narrow, such as less than 40 $\mu$m. Since the position signal from the potentiometer is an analog signal, theoretically its resolution of distance is infinite but, considering the signal stability and reliability, it is practically incapable of coping with the high distance resolution as mentioned above.

With a view to overcoming this problem, the inventors studied the possibility of replacing the potentiometer by an encoder as a position sensor for the ultrasound transducer or vibratory element. Encoders can be largely classified into: an absolute type which can detect an absolute position by means of a rotary disc having a detection pattern with a multitude of detection units in a predetermined pitch at predetermined angular intervals, in association with an optical or other sensor means adapted to produce pulse signals according to the number of detection units read in; and an increment type which can detect the occurrence and extent of a displacement but not the absolute position. The absolute encoder which is capable of detecting the absolute position can replace the potentiometer to a sufficient degree in terms of functions. However, in order to secure an extremely high resolution of distance, for example, a distance resolution of 40 $\mu$m or less, there has to be provided an encoder an objectionably large diameter along with an increased number of sensors in association with the detection pattern on the encoder disc. In addition to high resolution of distance, there has been a strong demand for the ultrasound transducer position sensor, which is usually mounted on a manipulating portion of an endoscope, to be compact and small in size and weight from the standpoint of the operationability of the endoscope. Accordingly, it is practically impossible to employ a large absolute encoder having high distance resolution of 40 $\mu$m or less. On the other hand, the incremental encoder which can detect displacement of the ultrasound transducer is not capable of detecting its position and thus cannot be applied to the transducer position sensor as it is.

SUMMARY OF THE INVENTION

The present invention contemplates to solve the above-mentioned drawbacks or problems of the prior art, and has its object the provision of an ultrasound internal examination system which is capable of detecting the position of an ultrasound vibratory element accurately with high resolution and in a stabilized manner.

It is another object of the present invention to provide an ultrasound internal examination system employing a position sensor mechanism of compact construction with reduced size and weight.

It is still another object of the present invention to provide an ultrasound internal examination system which is adapted to detect the exact position of the ultrasound vibratory element by the use of an incremental encoder.

In accordance with the present invention, there is provided for achieving the above-stated objectives, an ultrasound internal examination system which essentially includes: an ultrasound probe having an ultrasound vibratory element at the tip end of a flexible insert cable to be passed through a biopsy channel of an endoscope; an operating unit detachably mounted at the rear end of the biopsy channel of the endoscope and connected to a base end portion of the flexible cable; a probe operating member provided on the operating unit to scan the ultrasound vibratory member over a predetermined scanning range; an initial position sensor means for detecting the position of an initial point of the scanning range; and an incremental encoder adapted to generate pulse signals at a predetermined frequency upon detection of and during a displacement of the ultrasound vibratory element caused by the probe operating member.

The above and other objects, features and advantages of the invention will become apparent from the following description of preferred embodiments and the appended claims, taken in conjunction with the accompanying drawings which are given for the purpose of illustration only and should not be construed as limitative of the invention.

DESCRIPTION OF PREFERRED EMBODIMENTS

Now, the invention is described more particularly by way of the preferred embodiment shown in the drawings.

Figure 1:
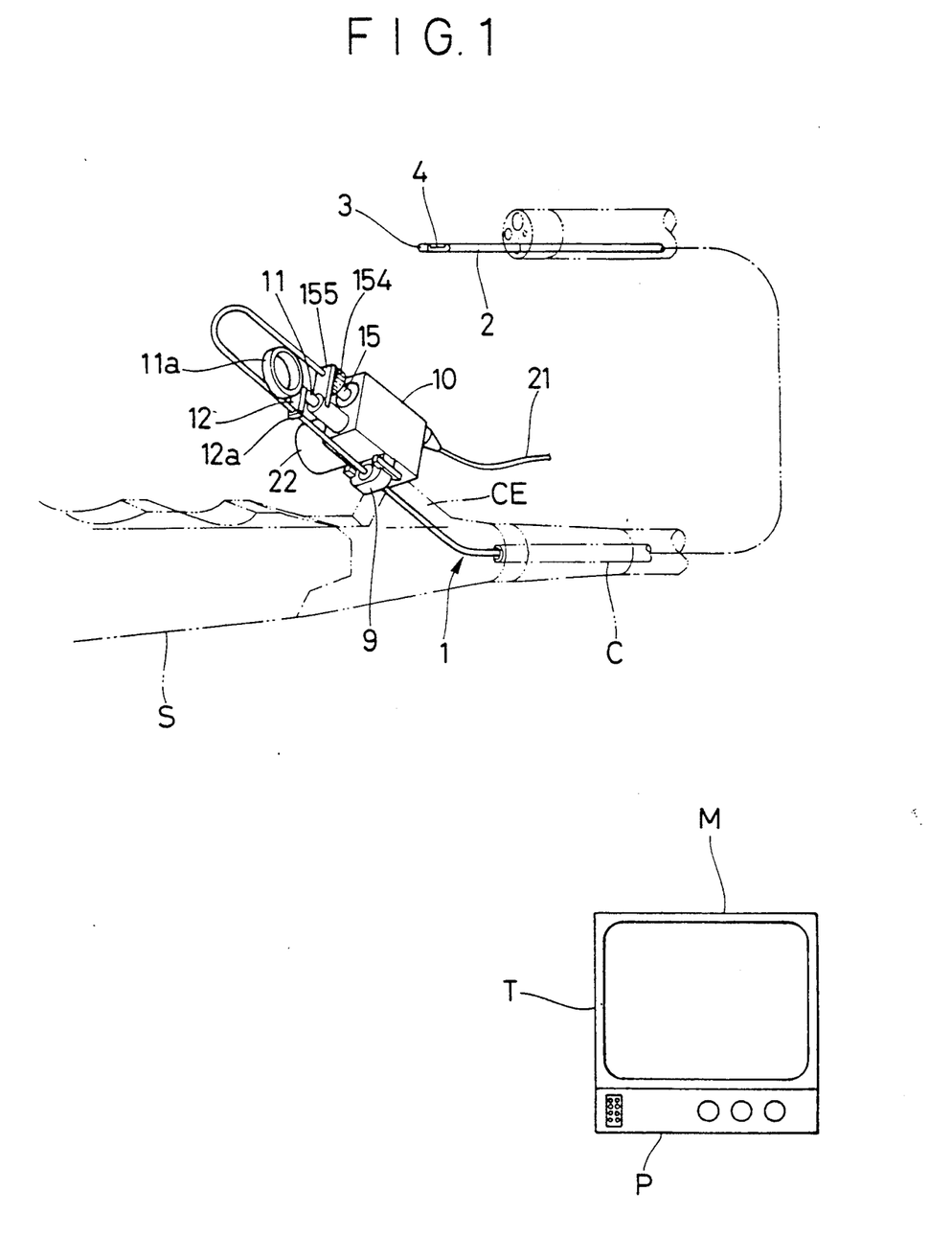
FIG. 1 is a schematic general view of an ultrasound internal examination system.

Referring to FIG. 1, there is illustrated the general arrangement of an ultrasound internal examination system, in which indicated at 1 is an ultrasound probe to be inserted to a point of ultrasound examination or diagnosis, for example, into a patient's body through a biopsy channel C of an endoscope S. For this purpose, the ultrasound probe 1 has a single-element ultrasound vibratory member 4 mounted in a rigid portion 3 at the tip end of a flexible cable 2.

The rigid portion 3 at the tip end of the ultrasound probe 1 is rotatable relative to the flexible insert cable 2. Active signal transmitting/receiving face 4a of the ultrasound vibratory member 4 on the rigid tip portion 3 is faced toward an opening which is formed at one side of the rigid tip portion 3. By displacing the ultrasound vibratory member 4 linearly in the axial direction, it is scanned over a predetermined range along an intracavitary wall portion to produce an ultrasound image of the cross section of wall tissues in the scanned range.

Figure 2:
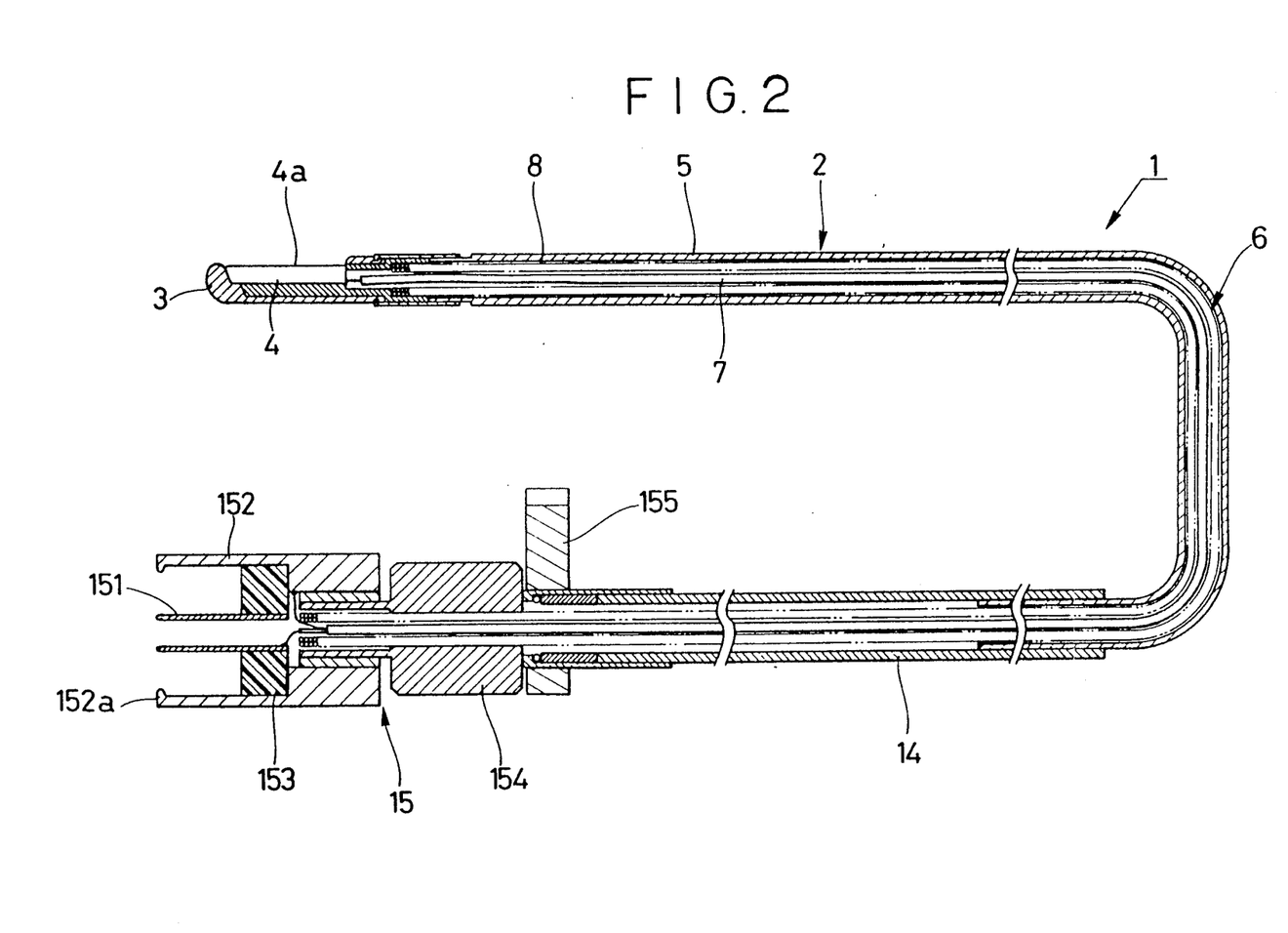
FIG. 2 is a longitudinal section of a flexible insert cable assembly of an ultrasound probe.

As shown particularly in FIG. 2, the flexible insert cable 2 has a flexible sleeve 5 consisting of a tube of a flexible slippery material like fluorine-type resin and accommodating a cable assembly 6. The cable assembly 6 has a function of transferring signals to and from the ultrasound vibratory member 4 along with a function of turning the rigid tip portion 3 by remote control for orientation of the ultrasound vibratory member 4. Therefore, the cable assembly 6 includes a coaxial cable containing a signal transfer line 7 and a couple of layers of coil springs 8 which are intimately fitted around the signal transfer line 7 and fixedly connected at the respective fore ends to the rigid tip member 3 to transmit thereto a propulsive force at the time of turning the ultrasound vibratory element 4.

Figure 3:
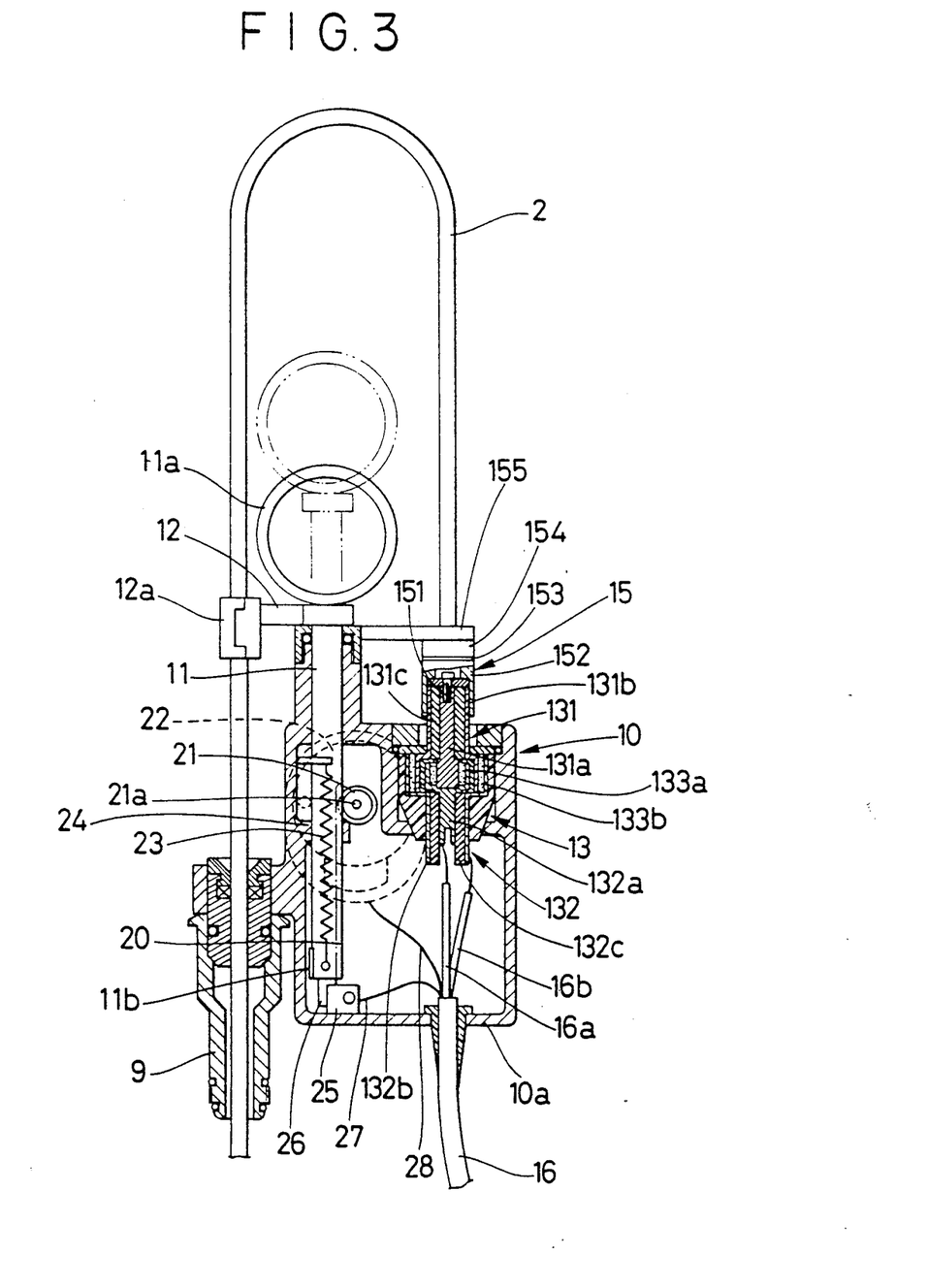
FIG. 3 is a schematic sectional view of an operating unit.

The flexible insert cable 2 of the ultrasound probe 1 is passed through a fitting member 9 to be attached to the rear end CE of the biopsy channel C, and detachably connected to an operating unit 10 which is in turn detachably connected to the fitting member 9. The flexible cable 2 can be pushed back and forth in the axial direction by means of the operating unit 10 to scan the ultrasound vibratory member 4 linearly over a predetermined range. For this purpose, as shown in FIG. 3, an operating rod 11, which serves as a probe operating means, is axially slidably mounted in casing 10a of the operating unit 10, the operating rod 11 being protruded out of the casing 10a to a predetermined extent. At the end which is protruded from the casing 10a, the operating rod 11 is provided with a finger hook 11a to be manipulated by a finger when pushing in or out the rod 11. Further, the operating rod 11 is contiguously provided with a connector arm 12 which is provided with a clamp portion 12a at its distal end for releasably holding a proximal end portion of the flexible cable 2, in such a manner that the proximal end portion of the cable 2 is looped over a certain length between the clamp portion 12a and a rotary connector 13 which is mounted on the casing 10a. The looped portion in the flexible cable 2 permits adjustment of the length of protrusion of the ultrasound probe 1 from the fore end of the biopsy channel C and, at the same time, its back and forth axial movements within a predetermined stroke range. The flexible cable 2 between the clamp portion 12a of the connecting arm 12 and the rotary connector 13 is sheathed in a sleeve 14 of relatively high pliability to stabilize the shape of the looped portion and to let the clamp portion 12 apply a clamping force sufficiently to hold the flexible cable 2 in fixed state against slippage which might otherwise occur when pulling the cable 2 back and forth.

In this instance, although the ultrasound probe 1 is designed for linear scanning, its base end is connected to the rotary connector 13 to permit adjustment of the ultrasound vibratory member 4 in the radial direction. With regard to the construction of the rotary connector 13, it is basically composed of a rotatable member 131 and a fixed member 132, the rotatable member 131 being coupled with the fixed member 132 rotatably relative to the latter. The rotatable member 131 is provided with a pair of electrodes 131a and 131b which are electrically insulated from each other by an interposed insulating member 131c. Similarly, the fixed member 132 is provided with a pair of electrodes 132a and 132b and an insulating member 132c which is interposed between the electrodes 132a and 132b. The electrodes 131a and 131b are electrically connected to the electrodes 132a and 132b through fluid contacts 133a and 133b of mercury or other conductive fluid, respectively.

The base end of the flexible cable 2 of the ultrasound probe 1 is connected to a coupling member 15 which is in turn detachably connected to the rotatable member 131 of the rotary connector 13. The coupling member 15 is provided with a pin 151 and a cylindrical socket portion 152, which are electrically insulated from each other by an insulating member 153. In coupled state, the pin 151 is inserted in the electrode 131a of the rotatable member 131 while the socket portion 152 is fitted on the electrode 131b, thereby establishing electric connection therebetween. In order to hold the coupling member 15 stably in coupled state without spontaneous disengagement from the rotatable member 131, the cylindrical socket portion 152 is provided with a rim 152a which engages in a groove (not shown) on the circumference of the electrode 131b. The socket portion 152 is provided integrally with a rotating block 154 to which the base ends of the coil springs 8 are secured. Accordingly, upon turning the rotating block 154 with fingers, the coil springs 8 are turned therewith and thus the ultrasound vibratory member 4 is rotationally driven and turned into a desired radial direction. For the purpose of preventing the sleeve 14 from following the rotation of the block 154 at the time of such a rotating operation, a bridge member 155 is securely fixed to the sleeve 14. Further, lead wires 16a and 16b are connected to the electrodes 132a and 132b of the fixed member 132, respectively.

As mentioned hereinbefore, when scanning the ultrasound vibratory member 4, ultrasound pulses are transmitted therefrom at predetermined intervals on every displacement of the ultrasound vibratory member 4 over a predetermined distance while receiving return echoes and transferring same to the signal processor P of the ultrasound image observation terminal T to process the signals and displaying an ultrasound image on the monitor M. Therefore, for use as a trigger of ultrasound pulse transmission and in order to determine the position of each acoustic line of the ultrasound image to be displayed on the monitor M, there is a necessity for obtaining a signal concerning the position of the ultrasound vibratory member 4. For this purpose, as shown also in FIG. 4, a position sensor mechanism for the ultrasound vibratory member 4 is provided in the casing 10a. Namely, the position sensor mechanism includes a rack 20 which is formed on the operating rod 11 within the casing 10a, a pinion 21 meshed with the rack 20 and supported on a rotational shaft 21a, and a rotary type incremental encoder 22 coupled with the pinion shaft 21a. With this arrangement, the position of the operating rod 11 is detected from the output signal of the encoder 22, which is sent to the ultrasound observation terminal T.

The operating rod 11 is constantly biased toward the position indicated by imaginary line in FIG. 3, by the action of a return spring 23. In this state, a stepped portion 11b which is formed at a fore end portion of the operating rod 11 is stopped by engagement with a slide guide portion 24 which is provided on the inner wall surface of the casing 10a. As the operating rod 11 is pushed into the casing 10a against the biasing force of the return spring 23 into the position of solid line in FIG. 3, the ultrasound vibratory member 4 at the tip end of the flexible cable 2 is protruded from the endoscope by a predetermined length. Upon pulling back the operating rod 11, the ultrasound vibratory member 4 is moved backward, scanning a range corresponding to the stroke length of the forward and backward reciprocating movements.

An optical sensor 25 is provided in the casing 10a to detect the end of the inward stroke of the operating rod 11 in cooperation with a light blocking plate 26 which is mounted on an inner end portion of the operating rod 11. The position where the light blocking plate 26 is detected by the optical sensor 25 is used as the position of initial scanning point, that is, the initial position of display of the ultrasound image on the monitor M.

In this regard, the range which is scanned by the ultrasound vibratory member 4 is, for example, about 20 mm in the linear direction, and ultrasound signals of about 500 pulses are transmitted from the ultrasound vibratory member 4 in that range. It follows that, since the ultrasound pulses are received at intervals of about 40 $\mu$m over that scanning range, the encoder 22 should have high resolution power for detection of such minute distances.

Figure 4:
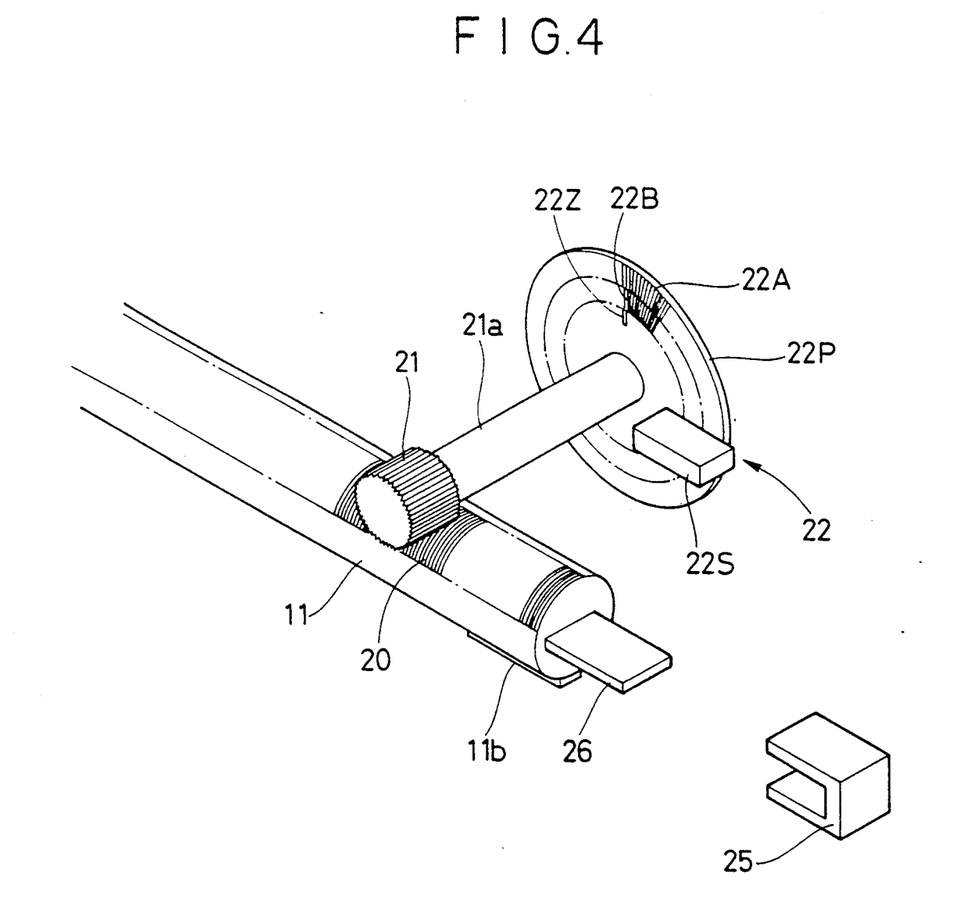
FIG. 4 is a schematic perspective view of a position sensor mechanism for the ultrasound vibratory element.

For this purpose, the encoder 22 is provided with an incremental encoder disc 22 with a couple of detection zones 22A and 22B of phase A and phase B each having an annular detection pattern of a predetermined pitch, a sensor assembly 22s having a couple of sensors disposed in face to face relation with the phase-A zone 22A and the phase-B zone 22B, respectively. In this instance, the pinion 21 is arranged to make a plural number of turns along the rack 20 within the scanning stroke range. This makes it possible to provide an encoder which has a small and compact construction and yet has a high resolution power. In case of an incremental encoder, one can know whether the rotation is in the incremental or decremental direction, on the basis of the phase difference between the phase-A zone 22A and the phase-B zone 22B. Accordingly, it is possible to detect how much the ultrasound vibratory member 4 has been displaced in the advancing or retracting direction.

However, a problem with the incremental encoder is that it cannot detect the absolute position of the ultrasound vibratory member 4, which is necessary for matching the position of the ultrasound vibratory member 4 with the initial display position of the ultrasound image on the monitor M. In this regard, in addition to the above-mentioned phase A and phase B zones, the encoder is provided with a phase Z which indicates the initial position of the ultrasound vibratory member 4. However, the phase-Z zone 22 Z cannot be used as a reference position because the encoder is arranged to make a plural number of turns in a scanning stroke of the ultrasound vibratory member 4. Therefore, the optical sensor 25 is employed to detect the end position of the inward stroke of the operating rod 11, using the output signal of the optical sensor 25 as a reference signal in producing a scan initiating signal for the monitor M.

Further, connected to the operating unit 10 is a cable 27 which connects the transmission/reception line 7 to the ultrasonic image observation terminal T, while supplying thereto the position signal indicative of the position of the ultrasonic vibratory member 4 through lead 28, which is connected to the encoder 22, and the initial position signal indicative of the initial point of the scanning stroke through lead 29 which is connected to the optical sensor 25.

The ultrasound image observation terminal T is largely composed of the signal processor P and monitor M. The signal processor P has a circuit arrangement as diagrammatically shown in FIG. 5. As clear from that figure, the signal processor P includes a transmission circuit 50 for transmitting ultrasound pulses from the ultrasound vibratory member 4, a reception circuit 51 for receiving return echo signal through the ultrasound vibratory member 4, and a position detection circuit 53 for producing a signal indicative of the position of the ultrasound vibratory member 4 on the basis of the output signals of the encoder 22 and optical sensor 25. The transmission circuit 50 is operated by a transmission trigger produced by a transmission/reception control circuit 54 to direct output pulses through the ultrasound vibratory member 4. The transmission/reception control circuit 54 is controlled according to a position signal which is produced at the output of the position detection circuit 53 with regard to the position of the ultrasound vibratory member 4. Namely, upon detecting from the output signal of the encoder 22 a predetermined extent of displacement of the ultrasound vibratory member 4, a transmission trigger is applied to the transmission circuit 50 from the transmission/reception control circuit 54 thereby triggering the transmission circuit 50 to direct ultrasound pulses to an internal portion under examination.

Figure 5:
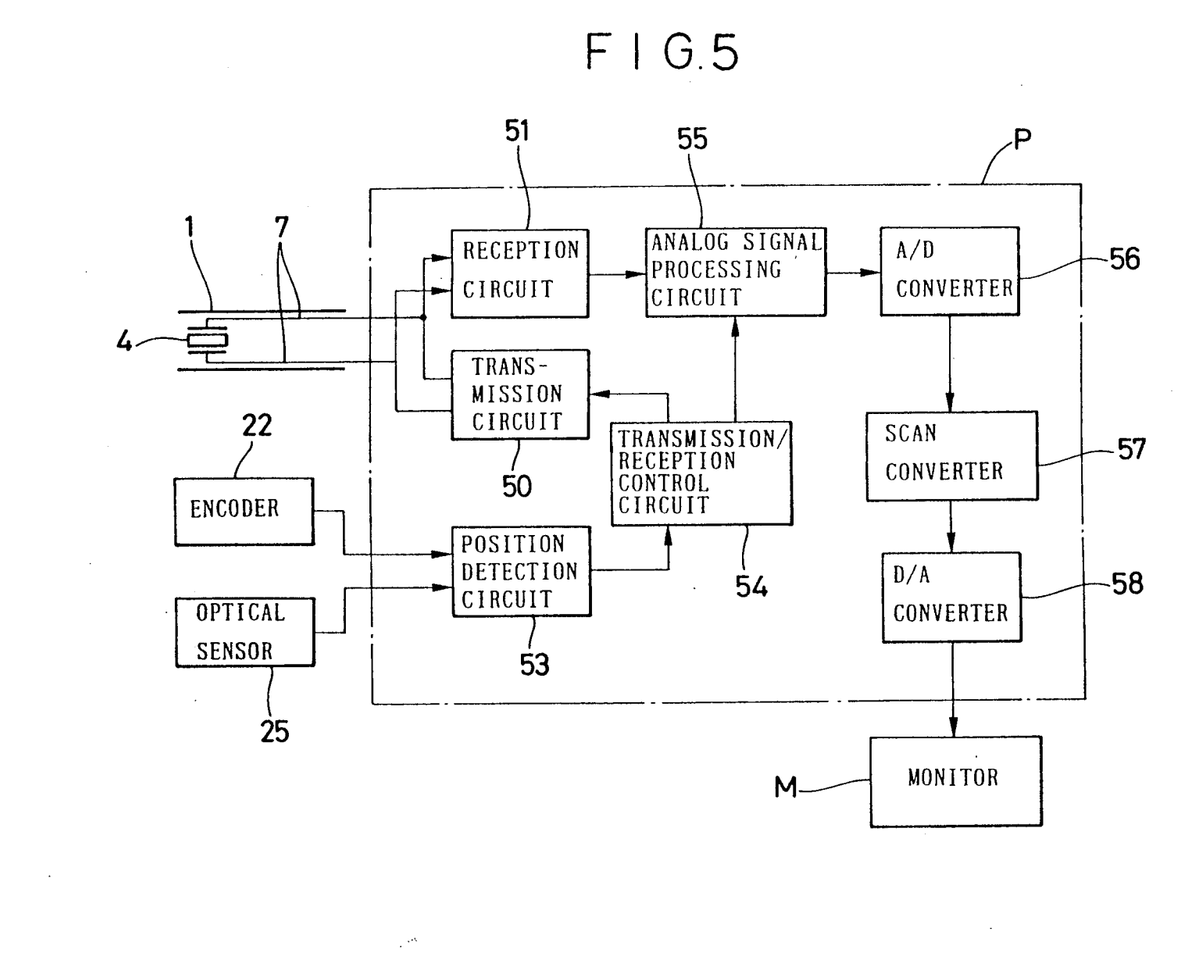
FIG. 5 is a block diagram of a signal processor of in an ultrasound image observation terminal.

The output of the reception circuit 51 is connected to an analog signal processing circuit 55, which is operated according to the signal from the transmission/reception control circuit 54 to process the ultrasound return signals from the reception circuit 51, including gain control, amplification, detection of the input signals and setting of addresses of display positions of processed signals on the monitor M. The processed signals are converted into digital signals through A/D converter 56 and stored in memory of a scan converter 57. One frame of image data, which is stored in the scan converter 57, is fed to the monitor M through a D/A converter 58 to display a linear ultrasonic image on the monitor.

The ultrasonic internal examination system of the above-construction is used, for example, for internal examination or diagnosis of a patient in the manner as follows. Firstly, the endoscope S is inserted into the patient's body in such a manner that its tip end is located at a target portion of examination or diagnosis. In this state, the operating unit 10 is fixed at the rear end CE of the biopsy channel C of the endoscope, and then the flexible insert cable 2 of the ultrasound probe 1 is passed through the biopsy channel C until the rigid tip portion 3 is protruded from the fore end of the endoscope S by a predetermined length. A rear end portion of the flexible cable 2 is fixed in the clamp 12a of the connecting arm 12, and the coupling member 15 at the rear end of the cable 2 is connected to the rotary connector 13, flexing the cable 2 in a looped form between the clamp member 12a and the rotary connector 13. Further, the cable 27 from the operating unit 10 is connected to the ultrasound image observation terminal T.

Now, under direct vision of the endoscope S, the rigid tip portion 3 of the flexible cable 2 is located at the target intracavitary wall portion to be examined or diagnosed, facing the active face 4a of the ultrasound vibratory member 4 toward the target wall portion. Then, if necessary, by turning the rotating block 154, the radial position of the ultrasound vibratory member 4 is adjusted to orient same exactly into a face-to-face or contacting position relative to the target portion. At this time, no twisting of the cable 27 takes place since the signal transmission/reception line 7 of the ultrasound probe 1 is connected to the cable 27 through the rotary connector 13 as described hereinbefore. Besides, signals are transferred smoothly between the line 7 and lead 16 which are connected through the fluid contacts 133a and 133b of the rotary connector 13, free of signal deteriorations or interference by external noises.

In this state, the finger hook portion 11a on the operating rod 11 is manipulated with a finger, firstly pushing in the rod 11 to block the light to the optical sensor 25 with the light blocking plate 26 at the inner end of the operating rod 11. Whereupon, the location of the ultrasound vibratory member 4 in the initial scanning position is detected to provide a signal of the initial position of display on the monitor M. Then, by the action of the return spring 23 or by pulling efforts of a finger, the operating rod 11 is moved outward to scan the ultrasound vibratory member 4 along the intracavitary wall portion. Concurrently, according to the extent of displacement of the operating rod 11, the pinion 21 is turned along the rack 20, producing pulse signals at the output of the encoder 22 at predetermined angular intervals of rotation. These pulses are supplied through the cable 27 to the signal processor P to determine, on the basis of the signal from the encoder 22 and the initial position signal from the optical sensor 25, a signal of the initial scanning position to be used as a trigger of ultrasound pulses. The ultrasound pulses are transmitted each time the ultrasound vibratory member 4 is displaced over a predetermined distance, while receiving the return echo signal through the ultrasound vibratory member 4. The received signal is sequentially sent to the signal processor P through the signal transfer line 7 of the cable assembly 6 and cable 27.

Figure 6:
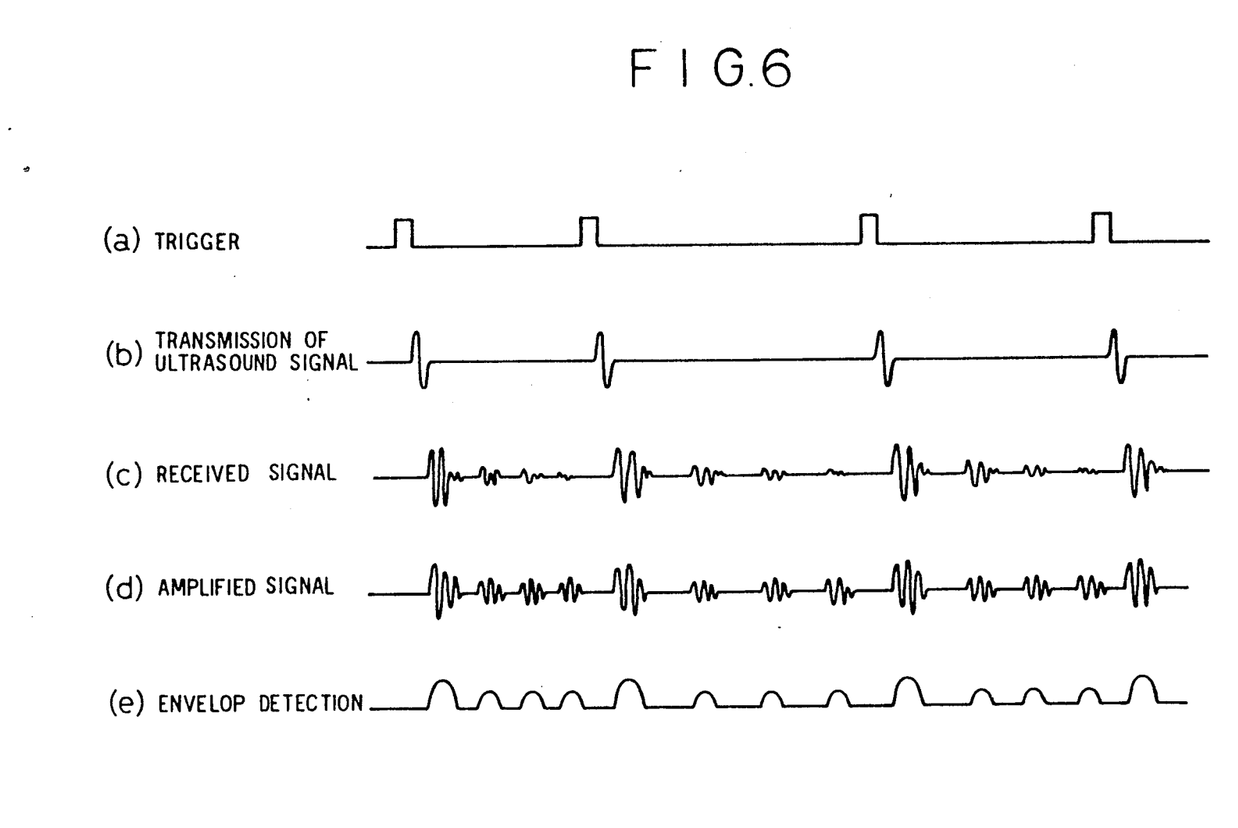
FIG. 6 is a diagram of signals processed by the signal processor.

More specifically, as the operating rod 11 is manipulated, the position detection signals are sequentially produced at the output of the encoder 22 and sent to the position detection circuit 53, which applies a trigger to the transmission circuit 50 as shown in FIG. 6(a) according to the position detection signal from the encoder 22, thereby triggering the ultrasound vibratory member 4 to transmit ultrasound pulses as shown at (b) of FIG. 6. The transmitted ultrasound signal is reflected at various depths of the cross-sectional area of the tissues under examination, and the reflected echoes are received by the ultrasound vibratory member 4 and sent to the reception circuit 51. The received signal has a waveform, for example, as shown in FIG. 6(c), which is amplified in the analog signal processing circuit 55 as shown at (d) of the same figure and, through envelop detection, shaped into the waveform as shown at (e). Simultaneously, on the basis of the signal from the transmission/reception control circuit 54, an address of display position is allotted to the signal of each acoustic line produced by the analog signal processing circuit 55. Further, the output signals of the analog signal processing circuit 55 are sequentially fed to the scan converter 57 through A/D converter 56. Thus, according to the scan position signal and ultrasound echo signal, an ultrasound image of the tissues of interest is displayed on the monitor M for examination or diagnostic purposes.

The above-mentioned position signal indicative of the position of the ultrasound vibratory member 4 is based on magnetic or optical pulse signal of the encoder 22, so that it is stable and less susceptible to disturbances by external causes such as fluctuations in supply voltage and noises, permitting smooth display of the above-mentioned ultrasound image. Besides, the encoder 22 is arranged to make a plural number of revolutions in the range of linear scanning of the ultrasound vibratory member 4, it becomes possible to attain extremely high resolution by the use of the small encoder 22 of an extremely minimized diameter. This contributes to provide the operating unit 10 of a compact form with reduced size and weight, which would not hinder the operation of the endoscope S even if the operating unit 10 is left on the endoscope S. Further, since the encoder 22 is capable of detections in both incremental and decremental directions, the scanning direction of the ultrasound vibratory member can be reversed in the middle of a scanning operation through the operating rod 11, for example, by pulling out the operating rod 11 in the middle of its inward stroke. Accordingly, a particular part of the scanning range can be repeatedly scanned for close examination.

As mentioned hereinbefore, the ultrasound probe 1 is designed to be inserted through a biopsy channel C of the endoscope S, so that there is naturally a dimensional difference between the outer diameter of the probe 1 and the inner diameter of the biopsy channel C. Therefore, at the bent portion of the endoscope S, the flexible cable 2 moves along the outer wall surface of the biopsy channel C when the ultrasound probe 1 is pushed in, and along the inner wall surface of the channel C when the probe 1 is pulled back. As a result, the operating rod 11 contains a certain invalid period at the initial point of its inward and outward strokes, where the ultrasound vibratory member 4 still remains unmoved. Since signals are supplied from the encoder 22 even in that period, an ultrasound image of the same position is displayed on the monitor M over a certain number of acoustic lines at the opposite ends of the scan stroke, spoiling the image accuracy at the stroke ends. This problem can be overcome by invalidating a certain number of encoder output signals when reversing the direction of the stroke of the operating rod 11.

We claim:
1. An ultrasound internal examination system, comprising:
   an ultrasound probe having an ultrasound vibratory element at a tip end of a flexible insert cable said probe being adapted to be passed through a biopsy channel of an endoscope;
   an operating unit detachably mounted at a rear end of said biopsy channel of said endoscope and connected to a base end portion of said flexible cable;
   a probe operating member provided on said operating unit to linearly scan over a stroke range said ultrasound vibratory member over a predetermined scanning range;
   an initial position sensor means for detecting the position of an initial point of said scanning range;
   an incremental encoder adapted to generate pulse signals at a predetermined frequency upon detection of and during a displacement of said ultrasound vibratory element by displacement of said probe operating member; and
   said incremental encoder comprising a rotary portion being capable of more than one revolution over said stroke range of said probe operating member in both incremental and decremental directions.

2. The ultrasound internal examination system as defined in claim 1, wherein said probe operating member is constituted by an operating rod arranged to be reciprocated within a predetermined stroke range, and connected to said flexible cable to scan said ultrasound vibratory member in a linear direction.

3. The ultrasound internal examination system as defined in claim 2, wherein said initial position sensor means is a sensor arranged to detect an inward stroke end of said operating rod.

4. The ultrasound internal examination system as defined in claim 3, said initial position sensor means includes a light blocking member fixed on an inner end of said operating rod, and an optical sensor adapted to detect said light blocking member.

* * * * *